United States Patent [19]

Frankel et al.

[11] Patent Number: 4,674,490

[45] Date of Patent: Jun. 23, 1987

[54] AUTOMATIC AEROSOL VACCINATION SYSTEM

[75] Inventors: Harry Frankel, Savyon; Jehuda Samberg, Haifa; Uri Bendheim, Moshav Shoresh; Jehudith Rivan, Rishon Le Zion; Mordechai Babazada, Moshav Petachiah, all of Israel

[73] Assignee: Volcani Research Center, Bet Dagan, Israel

[21] Appl. No.: 891,757

[22] Filed: Jul. 31, 1986

[30] Foreign Application Priority Data

| | | | |
|---|---|---|---|
| Aug. 1, 1985 | [IL] | Israel | 76001 |
| Apr. 22, 1986 | [IL] | Israel | 78589 |

[51] Int. Cl.[4] .............................................. A61M 11/00

[52] U.S. Cl. ................................ 128/200.14; 119/160

[58] Field of Search ....................... 128/200.14, 205.26, 128/1 B, 203.17, 203.27; 119/15, 160

[56] References Cited

U.S. PATENT DOCUMENTS

| | | | |
|---|---|---|---|
| 2,847,993 | 8/1958 | Woodruff | 128/205.26 |
| 2,984,240 | 5/1961 | Eames | 128/205.26 |
| 3,464,388 | 9/1969 | Stout | 119/15 |
| 3,924,571 | 12/1975 | Holman | 119/15 |
| 4,480,586 | 11/1984 | Lague et al. | 119/15 |

*Primary Examiner*—Henry J. Recla

*Attorney, Agent, or Firm*—Poms, Smith, Lande & Rose

[57] ABSTRACT

Apparatus for aerosol immunization of subjects such as day old chicks and the like including an aerosol exposure chamber having controlled humidity, apparatus for providing a precisely controlled spray of vaccine in the exposure chamber at a predetermined droplet median diameter and feed rate, apparatus for continuously supplying subjects, such as chicks and the like, to and removing them from the chamber for aerosol treatment, and apparatus for maintaining the relative humidity in the exposure chamber in the vicinity of 100% to prevent significant evaporation of water droplets containing the vaccine which could cause such droplets to shrink to within the respiration range of the subjects, thus harming them.

18 Claims, 2 Drawing Figures

AUTOMATIC AEROSOL VACCINATION SYSTEM

FIELD OF THE INVENTION

The present invention relates to vaccination techniques generally and more particularly to apparatus and techniques for aerosol vaccination.

BACKGROUND OF THE INVENTION

It is known to vaccinate day old chicks against Newcastle disease and bronchitis employing a combination of subcutaneous vaccination and simultaneous aerosol exposure.

Three types of supplementary aerosol vaccination methods have been proposed. One such method, hand spraying, is carried out with the aid of a small compression sprayer and employs a highly diluted spray usually containing about five doses per milliliter. The operator atomizes the spray fluid above and in the direction of boxes containing the chicks. This method has the disadvantage that functional spray parameters such as exposure time and application height are dependent on the operator and are not replicable. Furthermore, an ambient climatic condition such as relative humidity is not necesarily maintained constant and changes therein may produce changes in drop size due to evaporation.

Additionally, in some sprayers the pressure is not maintained constant, thus varying the droplet size spectrum and feed rate. In other sprayers, the droplet size is sufficiently small that a considerable part of the sprayed fluid is in drop sizes which are within the respiratory range of the chicks, that is, they are directly inhaled by the chick and probably reach the air bag system and the alveoli. The respiratory range for day old chicks is estimated to be particles having an aerodynamic diameter of less than 10–12 microns. This naturally causes vaccine to be wasted, and may cuase damage to the chicks.

A second method of supplementary aerosol spraying employs an automatic spray bar. This is a relatively automated technique wherein boxes, each containing approximately fifty chicks, are placed on a running belt and pass under a stationary spray bar. The output rate, spray height, exposure time, and range of droplet sizes are generally constant. However, ambient environmental conditions may vary and thus variations in the droplet size may occur, with the attendant possibility that droplets may fall within the respiratory range.

A third method of supplementary aerosol spraying employs a manually operated spray cell which is sized to accomodate a box containing about fifty chicks. A spray nozzle is affixed to the top of the cell and is fed with vaccine via a metering device, thus assuring a constant dose to the exposed chicks. The drop size range and its volume median diameter (VMD) is determined by the spray nozzle and its operating pressure. Although this method overcomes some of the difficulties mentioned above in connection with other methods, it does have the disadvantages that it is relatively wasteful in vaccine due to the use of a relatively large droplet VMD in order to avoid the harmful effects of evaporation, and further that it has a limited treatment capacity.

SUMMARY OF THE INVENTION

The present invention seeks to provide apparatus and methods for aerosol vaccination of chicks and the like which overcome the above-mentioned deficiencies of the prior art.

There is thus provided in accordance with a preferred embodiment of the present invention apparatus for aerosol immunization of subjects such as day old chicks and the like including an aerosol exposure chamber having controlled humidity, apparatus for providing a precisely controlled spray of vaccine in the exposure chamber at a predetermined droplet median diameter and feed rate, apparatus for continuously supplying subjects, such as chicks and the like, to and removing them from the chamber for aerosol treatment, and apparatus for maintaining the relative humidity in the exposure chamber in the vicinity of 100% to prevent significant evaporation of water droplets containing the vaccine which could cause such droplets to shrink to within the respiration range of the subjects, thus harming them.

In accordance with a preferred embodiment, of the present invention, the predetermined droplet median diameter is within the range of 40–100 micrometers in clouds and above 15 micrometers for mono-dispersed droplets.

Additionally in accordance with a preferred embodiment of the present invention, the apparatus for continuously supplying comprises an automatically controlled conveyor system for passing containers containing chicks into and out of the exposure chamber.

Further in accordance with a preferred embodiment of the present invention, there are provided pre and post-treatment chambers to minimize air movement into and out of the treatment chamber.

Additionally in accordance with a preferred embodiment of the present invention, the means for maintaining comprises means for supplying water to the exposure chamber via the spray providing means, and air circulation means, the former of which is provided for the purpose of increasing the humidity in the exposure chamber and the latter of which is provided for ensuring the equal distribution of moisture within the space of the exposure chamber.

Further in accordance with a preferred embodiment of the present invention, the air circulation means is operable simultaneously with operation of the means for supplying water and sequentially to operation of the means for vaccine spray provision.

Additionally in accordance with a preferred embodiment of the present invention, the air circulation means comprises at least one air blower.

Additionally in accordance with a preferred embodiment of the present invention there is provided a method for aerosol immunization of subjects comprising the steps of providing an aerosol exposure chamber having controlled temperature and humidity, providing a precisely controlled spray of vaccine in the exposure chamber, at a predetermined droplet median diameter and feed rate, continuously supplying subjects, such as chicks or the like, to and removing them from the chamber for aerosol treatment, and for maintaining the relative humidity of the exposure chamber in the vicinity of 100% to prevent significant evaporation of the vaccine containing droplets which could cause such droplets to shrink to within the respiration range and harm the subjects.

In accordance with a preferred embodiment of the present invention, the predetermined droplet median diameter is maintained within the range of 40–100 micrometers in clouds and above 15 micrometers for mono-dispersed droplets.

Additionally in accordance with a preferred embodiment of the present invention the maintaining step comprises the steps of supplying water to the exposure chamber via the spray providing means for the purpose of increasing the humidity in the exposure chamber and operation of the air circulation means, for ensuring the equal distribution of moisture within the space of the exposure chamber.

Further in accordance with a preferred embodiment of the present invention the air circulation means is operable simultaneously with operation of the means for supplying water and sequentially to operation of the means for vaccine spray provision.

Additionally in accordance with a preferred embodiment of the present invention the air circulation means comprises at least one air blower.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
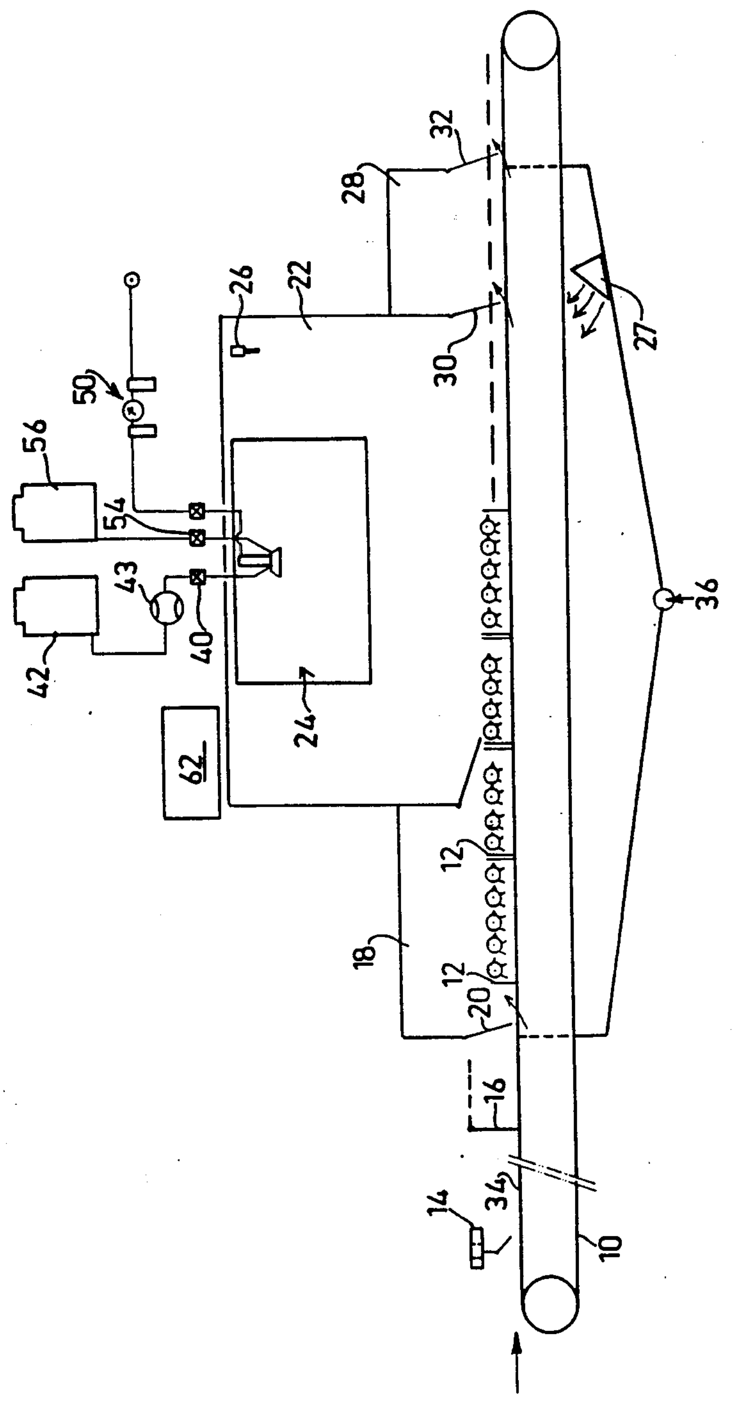
FIG. 1 is a diagrammatic illustration of an aerosol vaccination system constructed and operative in accordance with a preferred embodiment of the present invention.
Figure 2:
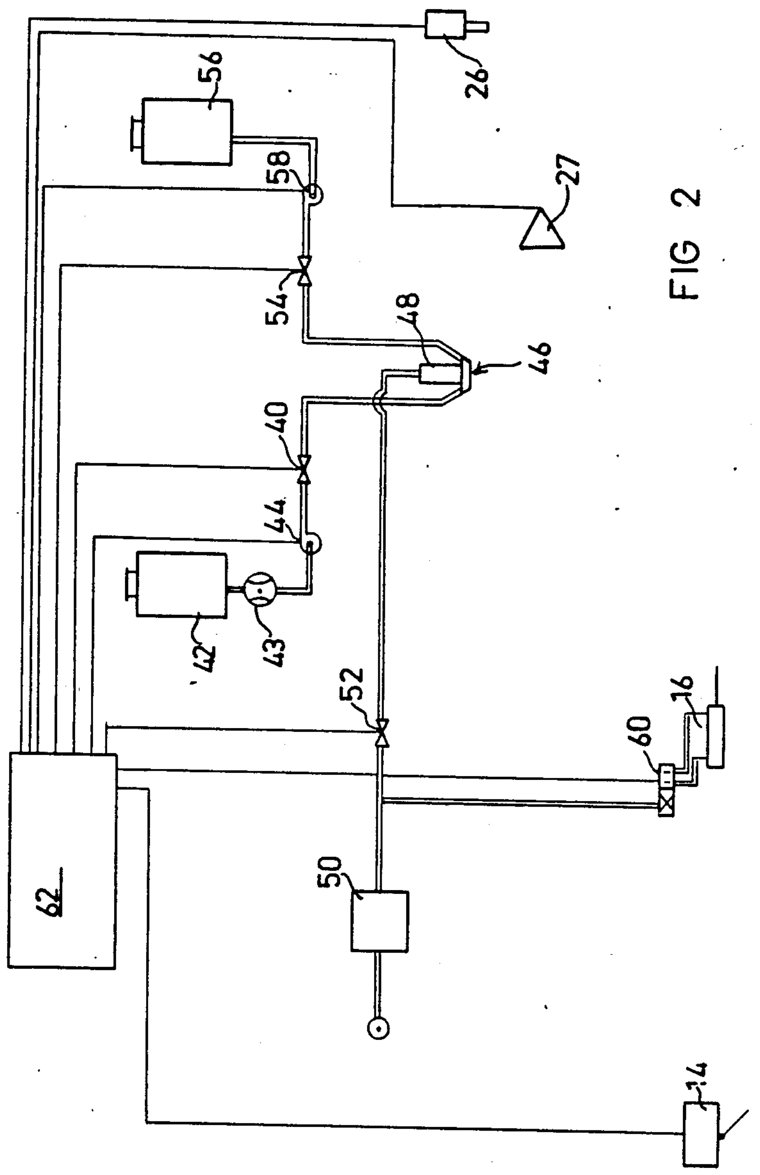
FIG. 2 is a detailed diagrammatic illustration of apparatus employed in an automatic vaccination system constructed and operative in accordance with a preferred embodiment of the present invention.

Reference is made to FIGS. 1 and 2, which illustrate an aerosol vaccination system constructed and operative in accordance with a preferred embodiment of the present invention. The system comprises a conveyor 10, which serves to convey boxed day old chicks or any other suitable subjects through the system.

The system of the invention will now be described from left to right along the conveyor 10. Boxes of chicks 12, each typically containing 50 chicks, are counted by an electromechanical counter 14, such as a Time Counter Control CX 400 sold by Eagle Signal Controls, Davenport, Iowa, U.S.A., and then engage a selectable stop member 16, the operation of which will be described hereinafter.

Downstream of selectable stop member 16 is a preexposure chamber 18 having an entry door 20. The pre-exposure chamber 18, which accomodates one box of chicks at a given time, leads to an exposure chamber 22, which is typically constructed to accomodate 4.5 boxes of chicks at a given time. The pre-exposure chamber 18 is provided in order to minimize the amount of ambient air flow to the exposure chamber 22 and to restrict the aerosol therewithin.

Exposure chamber 22 is provided with aerosol spray generating apparatus 24, which provides the vaccine carrying aerosol spray and which is also operative to provide desired humidification of the exposure chamber, which is monitored by a humidity sensor 26, such as a Rotronic Hygromer Model HTR, manufactured by Rotronic Ag. of Switzerland.

An air blower 27, the operation of which will be described hereinbelow, is provided to act in conjunction with the aerosol spray generating apparatus 24 and humidity sensor 26.

The boxed chicks which leave the exposure chamber 22 pass through a post-exposure chamber 28, which can accomodate one box of chicks at a given time and which also serves to minimize the amount of ambient air flow to the exposure chamber 22 and to restrict the aerosol spray within the exposure chamber. The post-exposure chamber 22 is provided with entry and exit doors 30 and 32, which, similarly to entry door 20 are opened by the passage of a chick-containing box therepast and otherwise generally seal the respective chambers.

The apparatus described generally hereinabove will be described in greater detail in connection with a description of the technique for vaccination of the present invention.

It is proposed, although not necessary, that prior to aerosol vaccination of the chicks, the chicks are first vaccinated by conventional subcutaneous or intramuscular techniques. Following this conventional immunization, aerosol vaccination according to the present invention takes place.

The overall length of the vaccination chambers 18, 22 and 28 is typically 290 cm along the longitudinal axis of the conveyor 10. Typically the pre-exposure chamber 18 extends about 60 cm, the exposure chamber 22, 150 cm and the post-exposure chamber 28, 80 cm. The width of each of the chambers typically is approximately 80 cm. The chambers are constructed to surround conveyor 10 passing therethrough such that the ceiling of the exposure chamber 22 lies about 100 cm above the conveyor surface 34 on which the chick boxes are supported and the ceilings of chambers 18 and 28 lie about 40 cm above the conveyor surface 34. The floor of all of the chambers is situated about 20–30 cm below surface 34 and is equipped with a drain 36 to facilitate cleaning.

In operation, a predetermined number of chick boxes, typically 20 in number, are assembled prior to commencement of aerosol vaccination. The boxes may be counted by an operator or alternatively automatically by counter 14.

When the requisite number of boxes have been assembled in side by side orientation along conveyor surface 34, and the sensed relative humidity in chamber 22 is at least at a predetermined level, such as 99.5 percent relative humidity, a solenoid valve 40 is opened, either manually or in response to the output of counter 14, and permits the flow of dilute vaccine from a reservoir 42, via a flow rate controller 43, by gravity or driven by a pump 44 to aerosol spray generating apparatus 24.

According to a preferred embodiment of the invention, the aerosol spray generating apparatus 24 comprises a kinetic energy nozzle 46 such as a spinning disc which is driven by a motor such as an air motor 48.

The spinning disc typically comprises a Part No. 4406 MINI ULVA, manufactured by Micron of England and is typically located 40 cm below the ceiling of chamber 22 and thus 60 cm above conveyor surface 34.

The air motor 48 is in turn driven by a source of pressurized air, past a pressure regulator 50, for providing a precisely determined rotation speed or motor 48, and a solenoid controlled valve 52, for governing on-off operation of the motor 48. Solenoid controlled valve 52 is operated just before solenoid valve 40 is opened in order to provide the desired aerosol spray due to impingement of the dilute vaccine at a predetermined flow rate on the spinning disc.

Should the sensed relative humidity be insufficient, solenoid controlled valve 52 is operated but solenoid valve 44 is not opened but instead a solenoid valve 54 is opened, approximtely 5 seconds after opening of valve 52 permitting distilled and sterilized water from a reservoir 56 to flow either by gravity or by action of a pump 58, to the spinning disc to provide an atomized mist of water for increasing the relative humidity of the exposure chamber 22.

In order to expedite the increase in relative humidity to a desired level throughout the exposure chamber 22 and to ensure equal distribution of moisture therein, air blower 27 is activated at approximately the same time as valve 54 is opened and is deactivated either simultaneously to the closing of valve 54 or at some desired time afterwards, but prior to the opening of valve 40. Air blower 27 is shown by way of example to be located on the floor of the chamber, but this is not necessarily so.

The precise location and number of air blowers 27 is important only in so far as the functioning thereof with regard to ensuring equal moisture distribution within chamber 22. Similarly, although air blower 27, in a preferred embodiment effects an air change of the air inside the chamber approximately three times per minute, any air blower that will function efficiently to ensure equal moisure distribution within chamber 22 may be used.

It should further be noted that conveying surface 10 is not necessarily continuous, but may instead comprise a plurality of parallel rods or the like, such that where air blower 27 is situated therebeneath, the function thereof is not necessarily adversely affected.

Once the requisite relative humidity is reached as confirmed by sensor 26, valve 54 may be closed manually or automatically and air blower 27 is similarly switched off, either simultaneously to the closing of valve 54 or at some desired time afterwards. It should be noted that valve 40 may not open until air blower 27 has been switched off.

As soon as both valve 54 is closed and air blowers 27 are deactivated, valve 40 may immediately be opened to produce the desired aerosol spray of vaccine, of precisely controlled volume median diameter. The volume median diameter is a function of the discs dimension and configuration, its speed of rotation, the properties of the liquid being atomized and the feed rate of the liquid to the disc.

At a predetermined time following opening of valve 40, which is sufficient to ensure that the droplet volume median diameter is as required, a piston or other suitable motive device 60 is energized to open selectable stop member 16 to permit entry of the chick boxes into the pre-exposure chamber 18 and the exposure chamber 22. Each box is exposed to the vaccine in the exposure chamber 22 for approximately 10.5 seconds. When the entire predetermined number of boxes has passed through the exposure chamber 22, valves 40 and 52 are closed, and the entire cycle begins anew.

Automatic or semiautomatic control apparatus 62 may be provided for automatic control of the apparatus and technique as described hereinabove. Such control apparatus is entirely conventional, including relays responsive to sensed conditions of humidity indicated by sensor 26, and counter outputs such as that from counter 14 as well as timers for determining various delays.

Alternatively, the control apparatus need not be provided and manual operation of the apparatus may be provided in response to displayed conditions, provided by suitable displays, not shown.

EXAMPLE

In an experimental device, boxes each containing about 50 chicks were exposed to diluted inactivated oil emulsion vaccine in conjunction with live Newcastle vaccine aerosol clouds produced at the rate of 30 ml/minute with VMDs (volume median diameters) varying over the range of 50–200 micrometers, under conditions which did not allow significant evaporation. The vaccination apparatus and technique provided good protection as tested by challenging with the Newcastle organism against which the vaccine was designed to protect. A dosage per chick of about one half the dosage conventionally used with subcutaneous or intramuscular injections was employed.

It will be appreciated by persons skilled in the art that the present invention is not limited to what has been particularly shown and described hereinabove. Rather the scope of the present invention is defined only by the claims which follow.

We claim:

1. Apparatus for aerosol immunization of subjects such as day old chicks and the like comprising:

- an aerosol exposure chamber having controlled humidity;
- means for providing a precisely controlled spray of vaccine droplets in said exposure chamber at a predetermined droplet mean diameter that would be outside of a size range of droplets that could normally be inhaled into the lung air bags and alveoli of the subjects and at a predetermined feed rate;
- means for supplying subjects, such as chicks or the like, to and removing them from said exposure chamber for aerosol treatment; and
- means for maintaining the relative humidity of the exposure chamber during operation in the vicinity of 100% to prevent significant evaporation of the vaccine droplets which could cause such droplets to fall within said respiration size range of the subjects and thus harm them.

2. Apparatus for aerosol immunization according to claim 1 and wherein said predetermined droplet mean diameter is within the range of 40–100 micrometers in clouds and above 12 micrometers for mono-dispersed droplets.

3. Apparatus for aerosol immunization according to claim 2 and wherein said means for supplying comprises an automatically controlled conveyor system for passing containers containing chicks into and out of the exposure chamber.

4. Apparatus for aerosol immunization according to claim 2 and also comprising pre and post-exposure chambers to minimize air movement into and out of the exposure chamber.

5. Apparatus for aerosol immunization according to claim 2 and wherein said means for maintaining comprises the following:

- means for supplying water to said exposure chamber via said spray providing means for increasing the humidity in said exposure chamber; and
- air circulation means for ensuring the equal distribution of moisture within the space of said exposure chamber.

6. Apparatus for aerosol immunization according to claim 1 and wherein said means for supplying comprises an automatically controlled conveyor system for passing containers containing chicks into and out of the exposure chamber.

7. Apparatus for aerosol immunization according to claim 1 and also comprising pre and post-exposure chambers to minimize air movement into and out of the exposure chamber.

8. Apparatus for aerosol immunization according to claim 1 and wherein said means for maintaining comprises the following:

means for supplying water to said exposure chamber via said spray providing means for increasing the humidity in said exposure chamber; and air circulation means for ensuring the equal distribution of moisture within the space of said exposure chamber.

9. Apparatus for aerosol immunization according to claim 8 and wherein said air circulation means is operable simultaneously with operation of said means for supplying water and sequentially to operation of said means for vaccine spray provision.

10. Apparatus for aerosol immunization according to claim 9 and wherein said air circulation means comprises at least one air blower.

11. Apparatus for aerosol immunization according to claim 8 and wherein said air circulation means comprises at least one air blower.

12. A method for aerosol immunization of subjects comprising the steps of:

providing an aerosol exposure chamber having controlled humidity;

providing a precisely controlled spray of vaccine droplets in said exposure chamber at a predetermined droplet means diameter that would be outside of a size range of droplets that could normally be inhaled into the lung air bags and alveoli of the subjects and at a predetermined feed rate;

supplying subjects, such as chicks or the like, to and removing them from said exposure chamber for aerosol treatment; and maintaining the relative humidity of the exposure chamber during operation in the vicinity of 100% to prevent significant evaporation of the vaccine droplets which could cause such droplets to fall within said respiration size range of the subjects and thus harm them.

13. A method according to claim 12 and wherein the predetermined droplet means diameter is maintained within the range of 40–100 micrometers in clouds and above 12 micrometers for mono-dispersed droplets.

14. A method according to claim 13 and wherein said maintaining step comprises the following steps:

the supplying of water to said exposure chamber via said spray providing means for increasing the humidity in said exposure chamber; and operation of air circulation means for ensuring the equal distribution of moisture within the space of said exposure chamber.

15. A method according to claim 12 and wherein said maintaining step comprises the following steps:

the supplying of water to said exposure chamber via said spray providing means for increasing the humidity in said exposure chamber; and operation of air circulation means for ensuring the equal distribution of moisture within the space of said exposure chamber.

16. A method according to claim 15 and wherein said air circulation means is operable simultaneously with operation of said means for supplying water and sequentially to operation of said means for vaccine spray provision.

17. A method according to claim 15 and wherein said air circulation means comprises at least one air blower.

18. A method according to claim 15 and wherein said air circulation means comprises at least one air blower.

* * * * *